(12) United States Patent
Zamponi et al.

(10) Patent No.: US 10,227,332 B2
(45) Date of Patent: Mar. 12, 2019

(54) T-TYPE CALCIUM CHANNEL MODULATOR AND USES THEREOF

(71) Applicants: UTI Limited Partnership, Calgary (CA); University of Montana, Missoula, MT (US)

(72) Inventors: Gerald Werner Zamponi, Calgary (CA); Philippe Diaz, Missoula, MT (US)

(73) Assignees: UTI LIMITED PARTNERSHIP, Calgary, Alberta (CA); THE UNIVERSITY OF MONTANA, Missoula, MT (US)

( * ) Notice: Subject to any disclaimer, the term of this patent is extended or adjusted under 35 U.S.C. 154(b) by 0 days.

(21) Appl. No.: 15/518,473

(22) PCT Filed: Oct. 15, 2015

(86) PCT No.: PCT/US2015/055757
§ 371 (c)(1),
(2) Date: Apr. 11, 2017

(87) PCT Pub. No.: WO2016/073160
PCT Pub. Date: May 12, 2016

(65) Prior Publication Data
US 2017/0233374 A1 Aug. 17, 2017

Related U.S. Application Data

(60) Provisional application No. 62/064,364, filed on Oct. 15, 2014.

(51) Int. Cl.
*C07D 209/88* (2006.01)
*C07D 403/12* (2006.01)
*C07D 401/12* (2006.01)

(52) U.S. Cl.
CPC ......... *C07D 403/12* (2013.01); *C07D 209/88* (2013.01); *C07D 401/12* (2013.01); *Y02P 20/55* (2015.11)

(58) Field of Classification Search
CPC .................................................. C07D 209/88
See application file for complete search history.

(56) References Cited

U.S. PATENT DOCUMENTS

| 6,399,631 B1 | 6/2002 | Elliot et al. |
| 8,586,619 B2 | 11/2013 | Wu et al. |
| 2004/0147752 A1 | 7/2004 | Rudolf et al. |
| 2012/0039804 A1 | 2/2012 | Diaz et al. |

OTHER PUBLICATIONS

Chemical Abstracts Registry No. 1007567-83-0, indexed in the Registry file on STN CAS Online on Mar. 12, 2008.*
Chemical Abstracts Registry No. 1492851-81-6, indexed in the Registry file on STN CAS Online Dec. 11, 2013.*
Chemical Abstracts Registry No. 53905-55-8, indexed in the Registry file on STN CAS Online Nov. 16, 1984.*
Chemical Abstracts Registry No. 1380048-66-7, indexed in the Registry file on STN CAS Online Jun. 25, 2012.*

* cited by examiner

*Primary Examiner* — Laura L Stockton
(74) *Attorney, Agent, or Firm* — Don D. Cha; Hamilton DeSanctis & Cha, LLP (57) ABSTRACT

The present invention provides T-type calcium channel modulators and methods for producing and using the same. In some embodiments, compounds of the invention are of the formula:

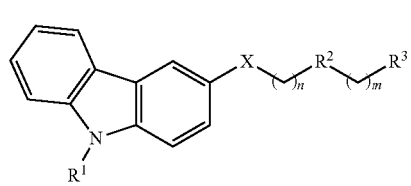

where
$R^1$ is selected from the group consisting of alkyl, alkenyl, polyether, alkoxy and cycloalkyl;
X is selected from the group consisting of methylene, $-C(=O)-[NR^4]_a-$, $-C(=S)-$, and $-S(=O)_b$;
$R^2$ is selected from the group consisting of heterocycloalkyl and heteroaryl;
$R^3$ is selected from the group consisting of alkyl, alkenyl, polyether, alkoxy, cycloalkyl, $-NR^5R^6$, $-C(=O)NR^5R^6$, $-C(=O)OR^a$ (where $R^a$ is alkyl, typically $C_1$-$C_8$ alkyl, often $C_2$-$C_6$ alkyl, and in one particular embodiment $R^a$ is tert-butyl), and $-SO_2NR^5R^6$;
$R^4$ is hydrogen, alkyl, or a nitrogen protecting group;
each of $R^5$ and $R^6$ are independently selected from the group consisting of hydrogen and alkyl;
a is 0 or 1;
b is 1 or 2;
n=1 to 3; and
m=0 to 1.

13 Claims, 5 Drawing Sheets

FIGURE 6. Reagents and conditions: (a) corresponding amine, EDAC, HOBt, DMAP, DIPEA, DCM, 0°C to rt.; (b) TFA, CH$_2$Cl$_2$; (c) N-tert-butyl-2-chloroacetamide, K$_2$CO$_3$, KI, n-butanol, reflux 3 h.

T-TYPE CALCIUM CHANNEL MODULATOR AND USES THEREOF

CROSS-REFERENCE TO RELATED APPLICATIONS

This application claims the priority benefit of U.S. Provisional Application No. 62/064,364, filed Oct. 15, 2014, which is incorporated herein by reference in its entirety.

FIELD OF THE INVENTION

The present invention relates to T-type calcium channel modulators and methods for producing and using the same. In some embodiments, compounds of the invention also have analgesic effects.

BACKGROUND OF THE INVENTION

T-type calcium channels are known for regulating neuronal and cardiac pacemaker activity. They open in response to small membrane depolarizations that in turn trigger the initiation of action potentials[1]. Disruption of this sensitive signaling mechanism often leads to hyperexcitability disorders such as arrhythmia, epilepsy and pain[2-8]. Similarly, up-regulation of T-type channels in primary afferent fibers has been linked to chronic pain disorders, whereas ablation of these channels mediates analgesia[3, 4, 7]. The development of new selective T-type channel antagonists has not been a trivial undertaking, with only a few such small organic molecules having recently been identified[5].

Therefore, there is a continuing need for compounds that can modulate T-type calcium channels.

SUMMARY OF THE INVENTION

Low-voltage-activated (T-type) calcium channels are important regulators of the transmission of nociceptive information in the primary afferent pathway and finding ligands (e.g., compounds) that modulate these channels is a key focus of the drug discovery field. Some aspects of the invention provide T-type calcium channel modulators. In some embodiments, compounds of the invention exhibit mixed cannabinoid receptor/T-type channel blocking activity. In other embodiments, compounds of the invention also exhibit analgesic effects in treatment of pain. Still in other embodiments, compounds of the invention exhibit selective Cav3.2 inhibitors without substantially influencing cannabinoid receptor activity. That is, compounds of the invention have $EC_{50}$ cannabinoid receptor activity of about 50 µM or more, typically about 100 µM or more, often about 250 µM or more and more often about 500 µM or more.

One particular aspect of the invention provides a compound of the formula:

I where $R^1$ is selected from the group consisting of alkyl, alkenyl, polyether, alkoxy and cycloalkyl; X is selected from the group consisting of methylene, —C(=O)—[$NR^4$]$_a$, —C(=S)—, and —S(=O)$_b$—; $R^2$ is selected from the group consisting of heterocycloalkylene and heteroarylene; $R^3$ is selected from the group consisting of alkyl, alkenyl, polyether, alkoxy, cycloalkyl, —$NR^5R^6$, —C(=O)$NR^5R^6$, —C(=O)—$OR^a$ (where $R^a$ is alkyl, typically $C_1$-$C_8$ alkyl, often $C_2$-$C_6$ alkyl, and in one particular embodiment $R^a$ is tert-butyl), and —$SO_2NR^5R^6$; $R^4$ is hydrogen, alkyl, or a nitrogen protecting group; each of $R^5$ and $R^6$ are independently selected from the group consisting of hydrogen and alkyl; a is 0 or 1; b is 1 or 2; n=1 to 3; and m=0 to 1.

As used herein, "alkyl" refers to a saturated linear monovalent hydrocarbon moiety of one to twenty, typically one to ten, and often two to eight carbon atoms or a saturated branched monovalent hydrocarbon moiety of three to twenty, typically three to ten, and often three to eight carbon atoms. Exemplary alkyl group include, but are not limited to, methyl, ethyl, n-propyl, 2-propyl, tert-butyl, pentyl, and the like. The term "alkenyl" refers to a linear monovalent hydrocarbon moiety of two to twenty, typically two to ten, and often two to eight carbon atoms or a branched monovalent hydrocarbon moiety of three to twenty, typically three to ten, and often three to eight carbon atoms having at least one carbon-carbon double bond. The term "alkoxy" means a moiety —OR where R is an alkyl as defined herein. The terms "heterocyclyl" and "heterocycloalkyl" are used interchangeably herein and refer to a non-aromatic monocyclic moiety of three to eight ring atoms in which one or more, typically one or three, and often one or two ring atoms are heteroatoms selected from N, O, or S(O)$_n$ (where n is an integer from 0 to 2), the remaining ring atoms being C, where one or two C atoms can optionally be a carbonyl group. The heterocyclyl ring can be optionally substituted independently with one or more, preferably one, two, or three, substituents. When two or more substituents are present in a heterocyclyl group, each substituent is independently selected. Exemplary substituents for heterocyclyl group include, but are not limited to, alkyl, haloalkyl, heteroalkyl, halo, nitro, cyano, optionally substituted phenyl, optionally substituted heteroaryl, optionally substituted phenylalkyl, optionally substituted heteroaralkyl, acyl, and the like. In particular, the term heterocycloalkyl includes, but is not limited to, tetrahydropyranyl, piperidino, piperazino, morpholino, pyrrolidino, thiomorpholino, thiomorpholino-1-oxide, thiomorpholino-1,1-dioxide, and the derivatives thereof. The term "cycloalkyl" refers to a saturated monovalent cyclic hydrocarbon moiety of three to seven ring carbons. The cycloalkyl may be optionally substituted independently with one, two, or three substituents selected from alkyl, haloalkyl, halo, nitro, cyano, heteroalkyl, optionally substituted phenyl, optionally substituted heteroaralkyl, or —C(O)R (where R is hydrogen, alkyl, haloalkyl, amino, monsubstituted amino, disubstituted amino, hydroxy, alkoxy, or optionally substituted phenyl). More specifically, the term cycloalkyl includes, for example, cyclopropyl, cyclopentyl, cyclohexyl, and the like. The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents, typically one or two substituents, selected from alkyl, haloalkyl, heteroalkyl, heterocyclyl, halo, nitro, cyano, carboxy, acyl, -(alkylene)$_n$-COOR (where n is 0 or 1 and R is hydrogen, alkyl, optionally substituted phenylalkyl, or optionally substituted heteroaralkyl), or -(alkylene)$_n$-CON$R^aR^b$ (where n is 0 or 1, and $R^a$ and $R^b$ are, independently of each other, hydrogen, alkyl, cycloalkyl, cycloalkylalkyl, hydroxyalkyl, aryl, or $R^a$ and $R^b$ together with the nitrogen atom to which they are attached form a heterocyclyl ring). More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like. "Protecting group" refers to a moiety, except alkyl groups, that when attached to a reactive group in a molecule masks, reduces or prevents that reactivity. Examples of protecting groups can be found in T.W. Greene and P.G.M. Wuts, *Protective Groups in Organic Synthesis*, $3^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. "Corresponding protecting group" means an appropriate protecting group corresponding to the heteroatom (i.e., N, O, P or S) to which it is attached. "A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The term "polyether" refers to a moiety of the formula —[O]$_x$—[(CH$_2$)$_y$—O]$_z$—$R^a$, where x is 0 or 1 (x is 0 for $R^1$); each y is independently an integer from 2 to 6, typically 2 to 5 and often 2 or 3; z is an integer from 1 to 20, typically 1 to 10, often 1 to 8, and most often 2 to 6; and $R^a$ is alkyl.

In some embodiments, $R^1$ is selected from the group consisting of alkyl, alkenyl, polyether, alkoxy and cycloalkyl; X is selected from the group consisting of methylene (i.e., CH$_2$), C(=O)—[NR$^4$]$_a$, C=S, S=O, SO$_2$; $R^2$ is selected from the group consisting of heterocycloalkyl and heteroaryl; $R^3$ is selected from the group consisting of alkyl, alkenyl, polyether, alkoxy, cycloalkyl, —NR$^5$R$^6$, —C(=O)NR$^5$R$^6$, and —SO$_2$NR$^5$R$^6$; $R^4$ is hydrogen, alkyl, or a nitrogen protecting group; each of $R^5$ and $R^6$ are independently selected from the group consisting of hydrogen and alkyl; a is 0 or 1; n=1 to 3; and m=0 to 1.

Yet in other embodiments, $R^1$ is selected from the group consisting of $C_1$-$C_{10}$ alkyl. Within these embodiments, in some instances, $R^1$ is propyl, butyl, or pentyl.

Still in other embodiments, X is C(=O)—[NR$^4$]$_a$. Within these embodiments, in some instances, a is 1. In other instances, n is 1. Still in other instances, $R^2$ is heterocycloalkyl. Within these instances, in some cases $R^2$ is piperidinyl or pyrrolidinyl. Yet in other instances, m is 1. Still in other instances, $R^3$ is selected from the group consisting of alkyl and —C(=O)NR$^5$R$^6$. Within these instances, in some cases, $R^3$ is iso-pentyl or —C(=O)NR$^5$R$^6$. Within such instances, in some cases, $R^5$ is hydrogen. Still in other cases, $R^6$ is alkyl. One particular $R^6$ is tert-butyl.

Still in other embodiments, Compound of Formula I is selected from the group consisting of:

; and

-continued

It should be appreciated that combinations of the various groups described herein form other embodiments. For example, in one particularly embodiment $R^1$ is propyl, butyl, or pentyl; X is C(=O)—[NR$^4$]$_a$, a is 1; n is 1; $R^2$ is piperidinyl or pyrrolidinyl; m is 1; $R^3$ is iso-pentyl or —C(=O)NR$^5$R$^6$; $R^5$ is hydrogen; and $R^6$ is tert-butyl. In this manner, a wide variety of specific compounds are encompassed within the scope of the invention.

Another aspect of the invention provides a method for treating a clinical condition associated with T-type calcium channel activation, said method comprising administering to a subject in need of such a treatment a therapeutically effective amount of a Compound of Formula I.

In some embodiments, said clinical condition associated with T-type calcium channel activation comprises acute inflammatory pain, tactile allodynia, diabetic neuropathy, pulmonary hypertension, chemotherapeutic induced neuropathy, chronic pain, diabetes, epilepsy, visceral pain, cancer pain, cardiac hypertrophy, or a combination thereof.

Yet in other embodiments, Compound of Formula I has cannabinoid receptor, and T-type calcium channel inhibitory activities.

DETAILED DESCRIPTION OF THE INVENTION

Many of the known organic molecules that have been shown to modulate T-type calcium channels have structures similar to endogenous anandamide-related molecules named lipoamino acids[6, 9]. Lipoamino acids are known to interact with T-type calcium channels and several are also closely related to endocannabinoids[6, 9]. Many of these T-type blockers also have shown to interact with cannabinoid (CB) receptors[6, 9].

The present inventors have previously shown that this mixed T-type/cannabinoid block has beneficial effects in inducing analgesia in animal models of inflammatory pain [6, 9]. However, interactions with CB receptors, particularly $CB_1$ receptors, can have side effects that may affect mood and memory, in addition to their known psychoactive effects. Synthetic T-type calcium channel antagonists based on substituted piperidines have been previously disclosed. In addition, the present inventors have previously synthesized and characterized a series of cannabinoid compounds with the primary structure bearing a carbazole scaffold [6, 9]. These compounds produced mixed cannabinoid receptor/T-type channel blockers that were found to be efficacious in animal models of inflammatory and neuropathic pain. Interestingly, from structure-activity relationships (SAR), it was determined that tertiary amines were important for Cav3.2 block [6, 9] and that the length of the linker attaching the tertiary amine to the carbazole scaffold affected binding to $CB_1$ and $CB_2$ receptors.[10] Some of these compounds appeared to preferentially and potently inhibit T-type channels in-vitro. Accordingly, some aspects of the invention provide compounds that are effective at blocking T-type calcium channels.

A wide variety of compounds were synthesized and were screened using whole-cell voltage clamp techniques to identify the most potent T-type calcium channel inhibitors. Compounds 9 and 10 were then characterized using radioligand binding assays to determine their affinity for CB1 and CB2 receptors. The structure-activity relationship and optimization studies have led to the discovery of selective T-type calcium channel blockers, e.g., compound 9. As used herein, the term "T-type calcium channel blocker" refers to a compound that can modulate, in particular inhibit or reduce activation of T-type calcium channels. In some embodiments, the $IC_{50}$ of compounds of the invention for inhibiting T-type calcium channel is about 10 μM or less, typically about 2 μM or less, and often about 1 μM or less. The term "about" refers to ±20%, typically ±10%, and often ±5% of the numeric value.

In one particular embodiment, Compound 9 was efficacious in mediating analgesia in mouse models of acute inflammatory pain and in reducing tactile allodynia in the partial nerve ligation model. This compound was shown to be substantially ineffective (i.e., no noticeable activity was observed) in Cav3.2 T-type calcium channel null mice at therapeutically relevant concentrations and it caused no significant motor deficits in open field tests. Taken together, these data reveal a novel class of compounds whose physiological and therapeutic actions are mediated through block of T-type calcium channels.

Still other aspects of the invention provide compounds of Formula 1 (FIG. 1) that comprise a carbazole scaffold with an added heterocyclic bearing a tertiary amine. As can be seen, some of the compounds of the invention include modified chain length attached to the nitrogen of the carbazole, the length of the linker between the amide bond and the heterocycle ring and/or introduction of a lipophilic moiety attached to the heterocycle. In one embodiment, the compounds were characterized in-vitro for their ability to blocking transiently expressed human Cav3.2 (hCav3.2) T-type calcium channels and tested their affinities for cannabinoid receptors. Compound 9 was also tested in mouse models of inflammatory and neuropathic pain, revealing potent analgesia by virtue of its T-type channel blocking ability.

Figure 6:
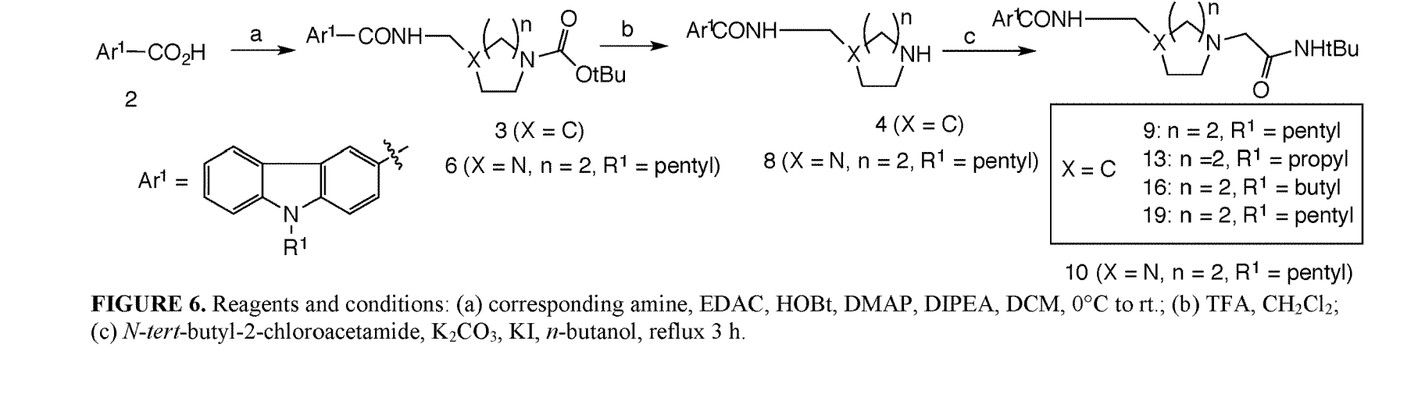
FIG. 6 shows one particular reaction scheme for producing some of the compounds of the invention.

Synthesis of Compounds of the Invention:

One particular synthesis of the carbazole derivatives is outline in FIG. 6. Amidation under standard peptide coupling conditions[10] of N-alkylated carbazole-3-carboxylic derivatives 2 with Boc-protected amines afforded the desired amide derivatives 3 and 6. Deprotection of the Boc protecting group in the presence of TFA in dichloromethane followed by alkylation of the resultant compounds 4 and 8 with N-tert-butyl-2-chloroacetamide provided the corresponding desired compounds 9, 10, 13, 16, and 19 (Table 1 and Table 2). Compound 20 was prepared by reductive amination of compound 4 using 3,3-dimethylbutyraldehyde (Table 2).

TABLE 1

Radioligand competitive binding assays (mean ± SEM) for carbazole-based analogues. Values are means of three experiments run in triplicate with standard deviation.

| No. | R1 | R2 | rCB1 $K_i^b$ (nM) | hCB2 $K_i^b$ (nM) |
|---|---|---|---|---|
| 5 | n-heptyl | -NH-CH2-(piperidin-4-yl)-N-Boc | n.b. (no observed binding) | n.b. |
| 6 | n-heptyl | -(piperazin-1-yl)-N-Boc | >5,000 | 2,957 ± 1,362 |
| 7 | n-heptyl | -NH-CH2-(piperidin-4-yl)-NH | n.b. | n.b. |
| 8 | n-heptyl | -(piperazin-1-yl)-NH | 283 ± 65 | 2,833 ± 1305 |
| 9 | n-heptyl | -NH-CH2-(piperidin-4-yl)-N-CH2-C(O)NH-tBu | >5,000 | >5,000 |
| 10 | n-heptyl | -(piperazin-1-yl)-N-CH2-C(O)NH-tBu | 15.0 ± 6.9 | 1,968 ± 906 |

TABLE 2

Analogues of compound 9: systematic variation in N-alkyl chain length and in the region occupied by the heterocycle.

| No. | R1 | R2 |
|-----|----|----|
| 13  | propyl | NH-CH2-(4-piperidinyl)-N-CH2-C(=O)-NH-tBu |
| 16  | butyl | NH-CH2-(4-piperidinyl)-N-CH2-C(=O)-NH-tBu |
| 19  | pentyl | NH-CH2-(3-pyrrolidinyl)-N-CH2-C(=O)-NH-tBu |
| 20  | pentyl | NH-CH2-(4-piperidinyl)-N-CH2-CH2-tBu |

Figure 1:
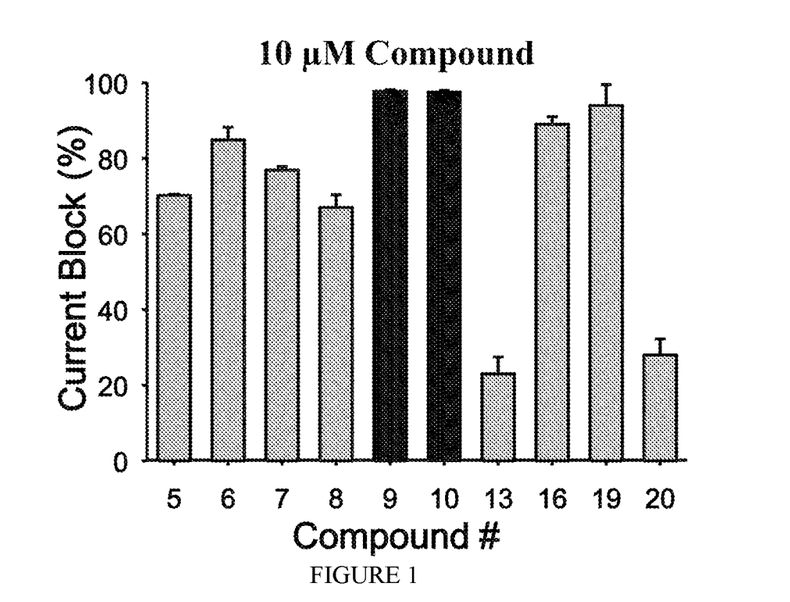
FIG. 1 shows results in percentage of whole cell current inhibition of human Cav3.2 (T-type) in response to 10 μM application of the compound series. For Cav3.2 channels, the holding and test potentials were respectively −110 and −20 mV.

In-Vitro Characterization of the Compound Series:

The compounds was screened using whole-cell voltage clamp techniques for their ability to mediate tonic block of transiently expressed hCav3.2 channels (FIG. 1). Next, radioligand binding assays were used to assess the affinities of these compounds for both $CB_1$ and $CB_2$ receptors (Table 1).

In the course of this work on the structure-activity relationship for this novel series of T-type channel blockers, the optimal linker length attached to the carbazole's carbonyl (FIG. 1) was studied. Various degrees of inhibition of these channels were observed, with compounds 9 and 10 being some of the most potent blockers of expressed hCav3.2. These two compounds mediated near complete inhibition at our standard test concentration of 10 µM (FIG. 1). Interestingly, both of these compounds are very similar in structure, with both having a cyclic tertiary amine attached to the carbazole scaffold (Table 1). It has been shown that this modification helps confer T-type channel blocking activity onto various organic molecules[6, 9], in agreement with data presented here.

As shown in Table 1, compound 10 showed high affinity binding to $CB_1$ receptors (15 nM), whereas its affinity for the $CB_2$ receptor was approximately 100-fold lower (2 Compound 9 however, did not bind to the two receptors with an affinity less than 5 µM for $CB_1$ and $CB_2$ respectively. One of the differences between compounds 9 and 10 is the elongated chain attached to the nitrogen of the carbazole in 9 (Table 1). This type of modification has been shown to alter cannabinoid receptor binding[6, 9, 10], but it has not been demonstrated whether this modification affects the interactions of these compounds with Cav3.2. Among the first series of compounds 5 to 10, replacement of a piperazine moiety by a methylpiperidine moiety appeared to be the most optimal for decreasing cannabinoid receptor affinity without impacting T-type calcium channel block. This difference in affinity for cannabinoid receptors between compounds bearing a piperazine moiety compared to a methylpiperidine moiety underscores the importance of chain length when developing compounds that selectively target T-type calcium channels over cannabinoid receptors.

The affect of chain length attached to the carbazole's endocyclic nitrogen (Table 2, compounds 9, 13 and 16) was also determined. Among the linear N-1 alkyl chains, a pentyl chain appeared to be optimal for occupying the T-type cavity, because systematically decreasing the length from n-pentyl in 9 negatively impacted the respective Cav3.2 blocking activities. Replacement of the piperidine ring by a pyrrolidine moiety (19) had a slight negative effect on Cav3.2 block, probably due to the lack of optimal ligand-receptor van der Waals contacts. Replacing the amide chain bored by the piperidine ring by an alkyl chain (20) significantly decreased the Cav3.2 block.

Figure 2:
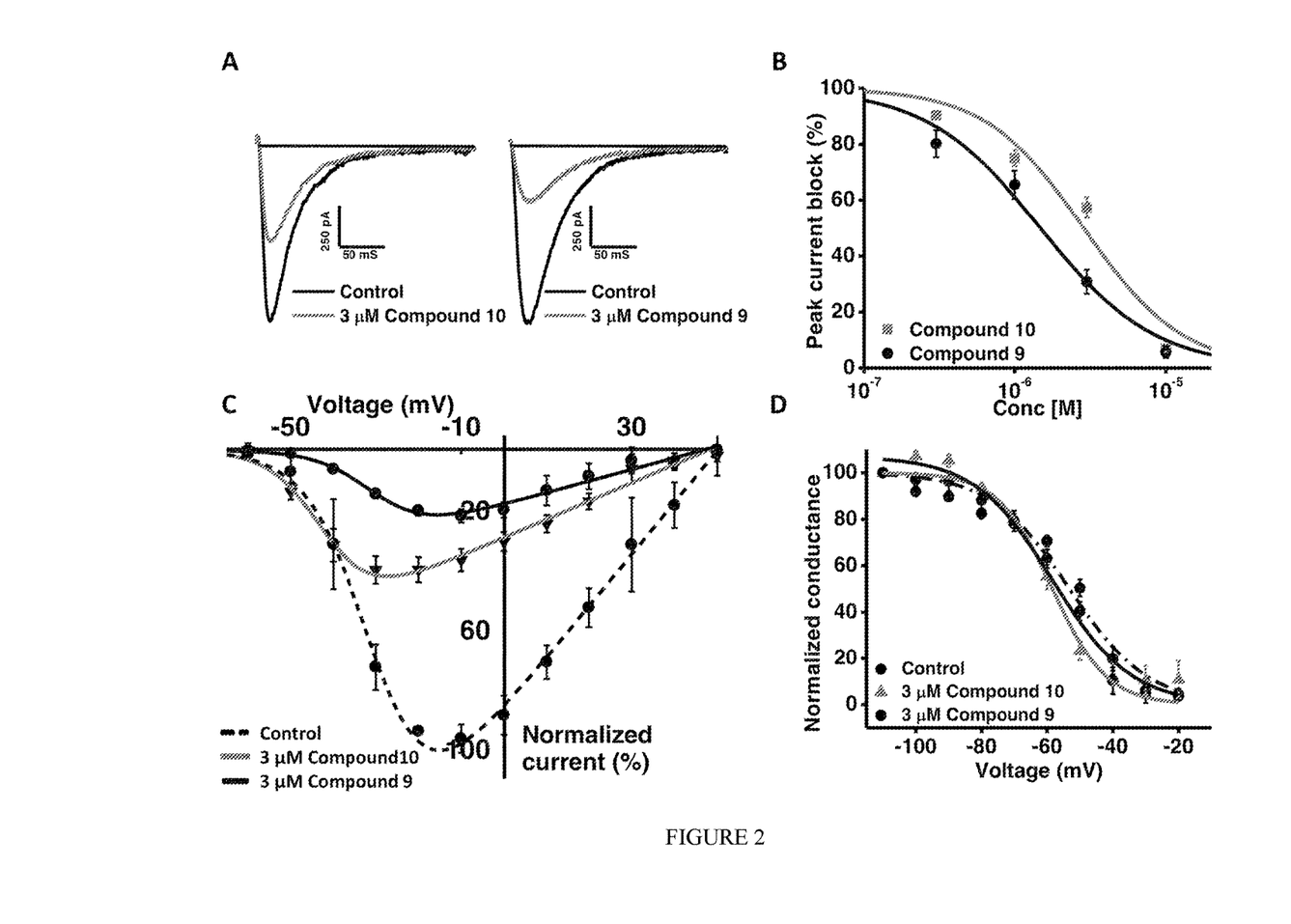
FIG. 2. Panel A shows representative traces of hCav 3.2 before and after application of 3 μM compounds 10 and 9 respectively. Panel B shows dose response relations for compound 9 and 10 block of hCav3.2 channels. The IC50 from the fit with the Hill equation was 1.48 and 3.68 μM respectively (n=6). Panel C shows effect of 3 μM compound 9 and 10 on the steady state inactivation curve for Cav3.2 channels. Paned D shows the effect of 3 μM compound 9 and 10 on the current voltage relation for Cav3.2 channels.

As can be seen in FIG. 2 panel A, the slight structural modification in 9 compared to 10 does indeed impact hCav3.2 channel inhibition. The affinity of 9 versus 10 increased more than two-fold with the $IC_{50}$ of 9 and 10 being 1.48 μM and 3.68 μM respectively (FIG. 2 panel B and Table 1). In addition, compound 10 shifted the half activation potential of hCav3.2 by −12 mV (FIG. 2 panel C and Table 1). There was no significant effect on half-inactivation potential (FIG. 2 panel D and Table 1).

Figure 3:
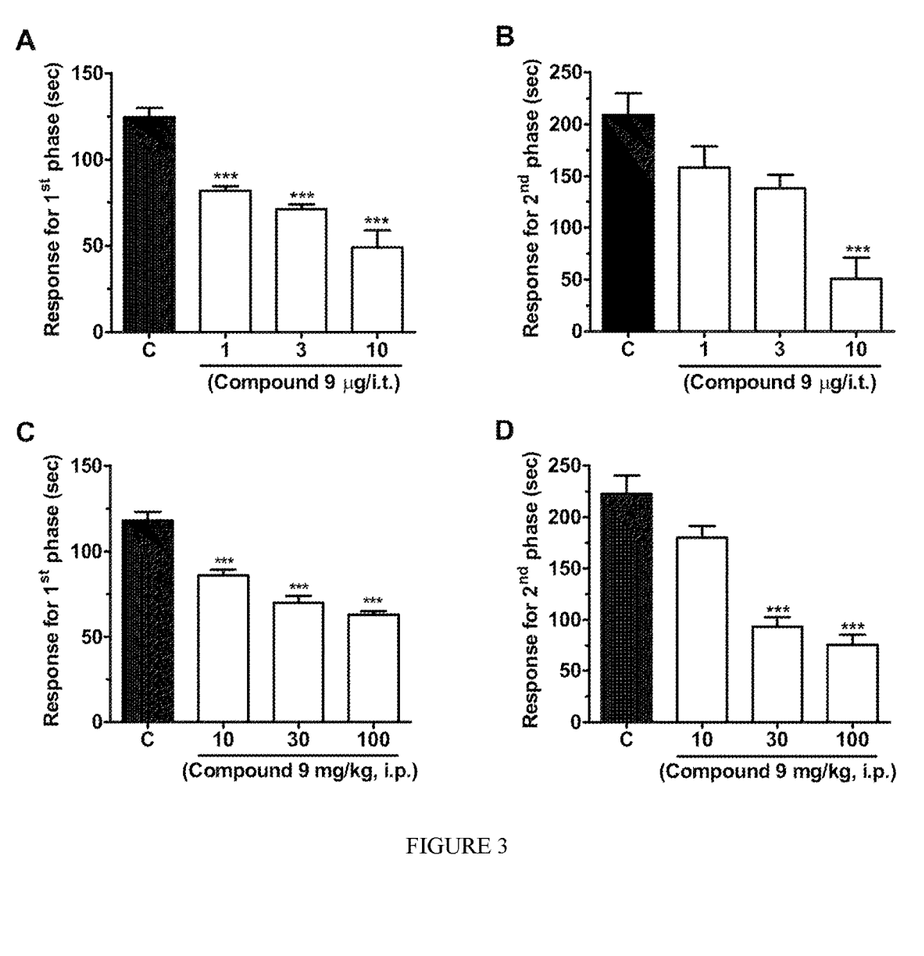
FIG. 3. Panels A and B shows effect of increasing doses of intrathecal compound 9 on the first and second phases of formalin-induced pain. Panels C and D show the effect of increasing doses of intraperitoneal compound 9 (on the first and second phases of formalin-induced pain.
Figure 4:
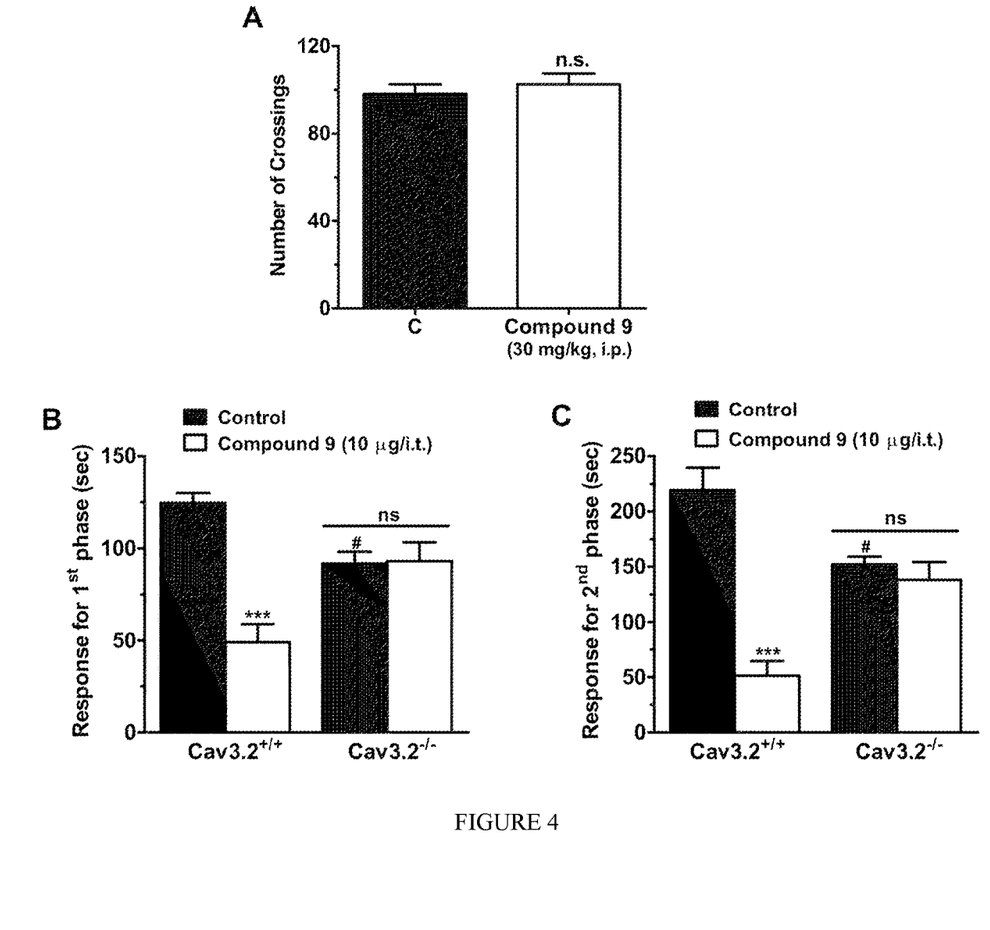
FIG. 4. Panel A shows effect of 30 mg/kg intraperitoneal compound 9 on locomotor activity of wild type mice in the open field test. Panels B and C shows comparison of effect of 10 μg/i.t. intrathecal compound 9 on the first and second phases of formalin-induced pain in wild type and Cav3.2 knockout mice respectively.

Effects of Compound 9 In-Vivo on Acute Pain:

Given the T-type channel blocking property of compound 9, it is believed that this compound can affect pain transmission in animal models. Compound 9 was delivered by either intrathecal (i.t.) or intraperitoneal (i.p.) routes and its effects on both the acute nociceptive and the slower inflammatory pain phases of the formalin test were evaluated. One-way ANOVA revealed that i.t. treatment of mice with compound 9 (1-10 μg/i.t., 20 minutes before) significantly decreased pain response time in both first (FIG. 3A) and second (FIG. 3 panel B) phases (61±8% and 76±10% inhibition, respectively). I.p. treatment of mice with compound 9 (10-100 mg/kg, i.p., 30 minutes prior) also resulted in significantly (one-way ANOVA) reduced pain response time in both the first (FIG. 3C) and second (FIG. 3 panel D) phases (47±2% and 66±48% inhibition, respectively). Importantly, systemic (via i.p.) treatment with compound 9 (30 mg/kg, i.p.) did not significantly affect locomotor activity of mice assessed via an open-field test (FIG. 4 panel A), suggesting that the reduced response times observed in the previous formalin tests were not due to altered motor behavior. In order to investigate if the effects observed for compound 9 were specifically mediated via T-type channels, a formalin test was performed in $Ca_v3.2$ null mice that were treated either with vehicle or with compound 9 (10 μg/i.t.). The $Ca_v3.2$ null mice exhibited a lower mean response time when compared to wild-type mice, which is in agreement with previous data[4, 6]. As indicated in FIG. 4 panels B and C, they appear to be substantially insensitive to i.t. treatment with compound 9 (10 μg i.t.) as revealed by two-way ANOVA, indicating that compound 9 mediates its analgesic effects specifically via T-type channels.

Figure 5:
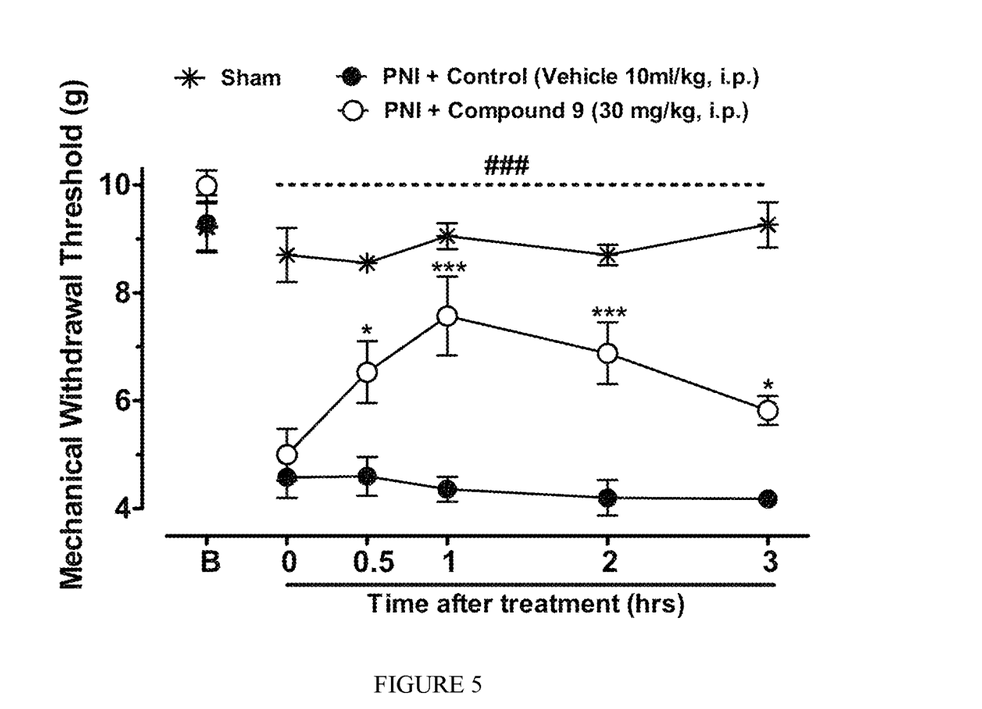
FIG. 5 shows the results of blind analyses of the time course of treatment of neuropathic mice with vehicle or compound 9.

Effect of Compound 9 on Chronic Neuropathic Pain:

To verify whether compound 9 modulates pain transmission under neuropathic conditions, mechanical withdrawal thresholds was analysed in mice with a partial sciatic nerve injury (PNI) and treated with compound 9 (30 mg/kg, i.p.) 14 days after nerve injury. As shown in FIG. 5, sciatic nerve injury triggers mechanical hyperalgesia as confirmed by significant decrease of mechanical withdrawal thresholds when compared to baselines levels (Pre-PNI, $P<0.001$). Two-way ANOVA revealed that systemic (i.p.) treatment of mice with compound 9 (30 mg/kg, i.p.) significantly attenuated the mechanical hyperalgesia induced by sciatic nerve injury when compared with the PNI+Control group for longer than 3 hours after treatment. These data indicate that compound 9 treatment modulates pain transmission and mediates analgesia in this animal model of chronic neuropathic pain.

TABLE 3

Biophysical parameters of hCav3.2 calcium channel in the absence and the presence of compound 10 and 9.

|  | $V_{0.5}$ act mV) 3 μM | Vh (mV) 3 μM | IC50 Tonic (μM) |
|---|---|---|---|
| Wt hCav3.2 | −30.0 | −53.1 ± 1.67 |  |
| Compound 9 | −29.7 | −58.2 ± 1.43 | 1.48 ± 0.2 |
| Compound 10 | −42.0* | −58.3 ± 1.31 | 3.68 ± 0.5 |

Discussion:

T-type calcium channels are important contributors to a range of physiological functions[11] and it is well established that they play important roles in the afferent pain pathway[2, 4, 5]. Finding specific and selective blockers of these channels has proven difficult as many of the well-known T-type channel blockers such as mibefradil or ethosuximide block other channels, which can then result in side effects[2]. The present invention provides compounds with structures similar to some of the endogenous ligands that are known to interact with T-type channels[6, 9]. In particular, compounds of the invention include structures that were modified to reduce their affinity for cannabinoid receptors while attempting to increase affinity for Cav3.2 channels. Thus, in some embodiments, compounds of the invention have reduced affinity for cannabinoid receptors while having increased affinity for Cav3.2 channels compared to, for example, mibefradil or ethosuximide.

In some embodiments, compounds of the invention are based on endogenous cannabinoid ligands that targeted both CB receptors and T-type calcium channels[6, 9]. Using data obtained from these experiments, additional compounds were designed with an extra substituted tertiary amine attached to the carbazole scaffold. The chain length attached to the carbazole to one of the compounds (compound 9) were then extended to improve its selectivity for T-type channels over CB receptors[6, 9], e.g., compared to mibefradil or ethosuximide. These data show that the length of the linker between the carbazole scaffold and the heterocyclic moiety is one of the key drug structural determinants that can be exploited to produce better and more selective T-type channel inhibitors. The observation that some compounds of the invention's analgesic actions were abolished upon removal of Cav3.2 channels indicates that the biological target for compound 9 in the context of pain signaling is Cav3.2. The potent effects of compound 9 on pain response in injured wild type animals fits with the notion that T-type channels play an important role in the afferent pain pathway [7, 8] and also with a number of previous studies showing that Cav3.2 channel blockers are efficacious in various pain models[2, 5].

Data presented herein suggest that using a carbazole scaffold is an effective strategy for developing potent, selective T-type calcium channel blockers for therapeutic intervention into inflammatory and neuropathic pain hypersensitivity. In addition, T-type channels are also associated with many other disorders, including epilepsy and cardiac hypertrophy[8], therefore the novel pharmacophores that are disclosed herein can be used towards treatment of these disorders.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

In Vitro Receptor Radioligand $CB_1$ and $CB_2$ Binding Studies:

$CB_1$ and $CB_2$ radioligand binding data were obtained using National Institute of Mental Health (NIMH) Psychoactive Drug Screening Program (PDSP) resources as described earlier[9].

cDNA Constructs:

Human Cav3.2 cDNA construct was obtained from the University of British Columbia (Vancouver, Canada).

tsA-201 Cell Culture and Transfection:

Human embryonic kidney tsA-201 cells were cultured and transfected using the calcium phosphate method as described previously. Transfected cells were then incubated 48 hours at 37° C. and 5% $CO_2$ and then re-suspended with 0.25% (w/v) trypsin-EDTA (Invitrogen) and plated on glass coverslips a minimum of 3 to 4 hours before patching.

Electrophysiology:

Whole-cell voltage-clamp recordings from tsA-201 cells were performed at room temperature 2 to 3 days after transfection. External recording solution contained (in mM): 114 CsCl, 20 BaCl2, 1 MgCl2, 10 HEPES, 10 Glucose, adjusted to pH 7.4 with CsOH. Internal patch pipette solution contained (in mM): 126.5 $CsMeSO_4$, 2 $MgCl_2$, 11 EGTA, 10 HEPES adjusted to pH 7.3 with CsOH. Internal solution was supplemented with 0.6 mM GTP and 2 mM ATP and mixed thoroughly just prior to use. Liquid junction potentials for the recording solutions were left uncorrected.

Tested compounds were prepared daily from DMSO stocks diluted in external solution. Using a custom built gravity driven micro-perfusion system, diluted compounds were then applied rapidly and locally to the cells. Control vehicle experiments were performed to ensure that 0.1% DMSO had no effect on current amplitudes or on the half-activation and half-inactivation potentials (data not shown). Currents were measured using the whole-cell patch clamp technique and an Axopatch 200B amplifier in combination with Clampex 9.2 software (Molecular Devices, Sunnyvale, Calif.). After establishing whole cell configuration, cellular capacitance was minimized using the amplifier's built-in analog compensation. Series resistance was compensated by at least 85% in all experiments. All data were digitized at 10 kHz with a Digidata 1320 interface (Molecular Devices) and filtered at 1 kHz (8-pole Bessel filter). Raw and online leak-subtracted data were both collected simultaneously. In current-voltage relation studies, the membrane potential was held at −110 mV and cells were depolarized from −80 to 20 mV in 10 mV increments. For steady-state inactivation studies, a 3.6 second conditioning pre-pulse of various magnitude (initial holding at −110 mV), was followed by a depolarizing pulse to −20 mV. Individual sweeps were separated by 12 seconds to permit recovery from inactivation between conditioning pulses. The duration of the test pulse was typically 200 ms and the current amplitude obtained from each test pulse was normalized to that observed at the holding potential of −110 mV.

Animals:

During experiments, all efforts were made to minimize animal suffering according to the policies and recommendations of the International Association for the Study of Pain and all protocols used were approved by the Institutional Animal Care and Use Committee. For all experiments, either adult male C57BL/6J (wild-type) or CACNA1H knockout (Cav3.2 null) mice (20-25 g) purchased from Jackson Laboratories were used. There were a maximum of five mice per cage (30×20×15 cm) and access to food and water was unlimited. Temperature was kept at 23±1° C. on a 12 h light/dark cycle (lights on at 7:00 a.m.). Intraperitoneal (i.p.) injections of drugs were a constant volume of 10 ml/kg body weight. Intrathecal (i.t.) injections used volumes of 10 µl and were performed using the method described previously and carried out routinely in our laboratory. All drugs were dissolved in 1% or less DMSO, whereas control animals received PBS+1% DMSO. For each test, a different group of mice were used and only one experiment per mouse was performed. In experiments examining the action of compound 9 on PNI-induced neuropathy, the observer was blind to the conditions tested.

Formalin Test:

Before experiments were performed, mice were left to acclimatize for at least 60 minutes. Animals were then injected intraplantarily (i.pl.) in the ventral surface of the right hindpaw with 20 µl of a formalin solution (1.25%) made up in PBS. Following i.pl. injections of formalin, individual animals were placed immediately into observation chambers and monitored from 0-5 min (acute nociceptive phase) and 15-30 min (inflammatory phase). The time spent licking or biting the injected paw was then considered as a nociceptive response and recorded with a chronometer. compound 9 was delivered by i.t. (20 minutes prior) or by i.p. (30 minutes prior) and its effect on both the nociceptive and inflammatory phases of the formalin test was evaluated.

Open-Field Test:

Animals received compound 9 via i.p. (30 mg/kg) route 30 minutes before testing and the ambulatory behavior of the treated animals was assessed in an open-field test as described previously. Briefly, the apparatus consisted of a wooden box measuring 40×60×50 cm with a glass front wall. The floor was divided into 12 equal squares and the entire apparatus was placed in a sound free room. Animals were placed in the rear left square and left to explore freely and the number of squares crossed with all paws (crossing) in a 6 minute timeframe was counted. After each individual mouse session, the apparatus was then cleaned and dried with a 10% alcohol solution.

Partial Sciatic Nerve Injury (PNI)-Induced Neuropathic Pain:

Before surgery, mice were anaesthetised with isoflurane (5% induction, 2.5% maintenance). Partial ligation of the sciatic nerve was performed by tying the distal ⅓ to ½ of the dorsal portion as previously described. In sham-operated mice, the sciatic nerve was exposed without ligation and all wounds were closed and treated with iodine solution. After fourteen days post surgery, mice received either compound 9 (30 mg/kg, i.p.) treatment or vehicle, while sham-operated animals received only vehicle (10 ml/kg, i.p.). Mechanical hyperalgesia was then evaluated in a time-dependant manner.

Evaluation of Mechanical Hyperalgesia:

Mechanical hyperalgesia responses were recorded immediately before the surgeries (baselines), 14 days after the surgeries (0) and at various time points (0.5, 1, 2, 3 h) after treatment. Measurements were made using a Dynamic Plantar Aesthesiometer (DPA, Ugo Basile, Varese, Italy). Briefly, individual animals were placed in small enclosed testing arenas (20 cm×18.5 cm×13 cm, length×width×height) on top of a wire mesh floor and allowed to acclimate for a period of at least 90 minutes. The DPA device was then positioned so that the filament was directly under the plantar surface of the ipsilateral hind paw of the animal and tested three times per session.

Data Analysis and Statistics:

Data were analyzed using Clampfit 9.2 (Molecular Devices). Origin 7.5 software (Northampton, Mass., USA) was used in the preparation of all figures and curve fittings. Current-voltage relationships were fitted with the modified Boltzmann equation: $I=[G_{max}*(V_m-E_{rev})]/[1+\exp((V_{0.5act}-V_m)/k_a)]$, where $V_m$ is the test potential, $V_{0.5act}$ is the half-activation potential, $E_{rev}$ is the reversal potential, $G_{max}$ is the maximum slope conductance, and $k_a$ reflects the slope of the activation curve. Steady-state inactivation curves were fitted using the Boltzmann equation: I=1/(1+exp((Vm−Vh)/k)), where Vh is the half-inactivation potential and k is the slope factor. Dose-response curves were fitted with the equation y=A2+(A1−A2)/(1+([C]/IC50)$^n$) where A1 is initial current amplitude and A2 is the current amplitude at saturating drug concentrations, [C] is the drug concentration and n is the Hill coefficient. Statistical significance was determined by paired or unpaired Student's t-tests and one-way or repeated measures ANOVA, followed by Dunnett's test or Tukey's Multiple Comparison tests. Significant values were set as indicated in the text and figure legends. All data are given as means+/−standard errors.

Synthesis of Compounds:

All moisture sensitive reactions were performed in an inert, dry atmosphere of argon in flame dried glassware. Air sensitive liquids were transferred via syringe or cannula through rubber septa. Reagent grade solvents were used for extraction and flash chromatography. THF was distilled from Na/benzophenone under argon; dichloromethane ($CH_2Cl_2$) and chloroform ($CHCl_3$) were distilled from $CaH_2$ under argon. All other reagents and solvents which were purchased from commercial sources were used directly without further purification. The progress of reactions was checked by analytical thin-layer chromatography (Sorbent Technologies, Silica G TLC plates w/UV 254). The plates were visualized first with UV illumination followed by charring with ninhydrin (0.3% ninhydrin (w/v), 97:3 EtOH-AcOH). Flash column chromatography was performed using prepacked Biotage SNAP cartridges on a Biotage Isolera One instrument. The solvent compositions reported for all chromatographic separations are on a volume/volume (v/v) basis. $^1$HNMR spectra were recorded at 400 or 500 MHz and are reported in parts per million (ppm) on the δ scale relative to tetramethylsilane as an internal standard. $^{13}$CNMR spectra were recorded at 100 or 125 MHz and are reported in parts per million (ppm) on the δ scale relative to $CDCl_3$ (δ 77.00). Melting points were determined on a Stuart melting point apparatus from Bibby Scientific Limited and are uncorrected. High Resolution mass spectrometry (HRMS) was performed on a Waters/Micromass LCT-TOF instrument. All compounds were more than 95% pure.

N-((1-(2-(tert-butylamino)-2-oxoethyl)piperidin-4-yl)methyl)-9-pentyl-9H-carbazole-3-carboxamide (9)

Under nitrogen atmosphere, a mixture of 9-Pentyl-N-(piperidin-4-ylmethyl)-9H-carbazole-3-carboxamide 7[6] (389 mg, 1.03 mmol), N-tert-butyl-2-chloroacetamide (185 mg, 1.24 mmol), potassium carbonate (427 mg, 3.09 mmol), and potassium iodide (160 mg, 0.96 mmol) in n-butanol (5 mL) was subjected to microwave irradiation at 110° C. for 3 h. The mixture was allowed to cool to room temperature, diluted with DCM (50 mL) and filtered. The organic solvents were evaporated in vacuo. The residue was purified on a Biotage® KP-NH cartridge (amino-modified silica gel) using cyclohexane/EtOAc in different proportions to afford the title compound as a light yellow glass. Yield: 476 mg (94%). $^1$H NMR (400 MHz, $CDCl_3$) δ 8.49 (d, J=1.3 Hz, 1H), 8.01 (d, J=7.7 Hz, 1H), 7.84 (dd, J=8.6, 1.6 Hz, 1H), 7.41 (ddd, J=8.3, 7.1, 1.2 Hz, 1H), 7.33 (d, J=8.2 Hz, 1H), 7.29 (d, J=8.6 Hz, 1H), 7.16 (ddd, J=8.0, 7.1, 1.0 Hz, 1H), 7.00 (br s, 1H), 6.58 (t, J=5.8 Hz, 1H), 4.19 (t, J=7.2 Hz, 2H), 3.34 (t, J=6.5 Hz, 2H), 2.81-2.67 (m, 4H), 2.00 (td, J=11.7, 2.5 Hz, 2H), 1.83-1.74 (m, 2H), 1.71 (br d, J=13.9 Hz, 2H), 1.64-1.48 (m, 1H), 1.31-1.22 (m, 15H), 0.78 (t, J=6.9 Hz, 3H). $^{13}$C and DEPT NMR (101 MHz, $CDCl_3$) δ 169.84 (C=O), 168.52 (C=O), 142.33 (C), 141.15 (C), 126.44 (CH), 125.28 (C), 124.81 (CH), 122.96 (C), 122.73 (C), 120.68 (CH), 119.85 (CH), 119.68 (CH), 109.23 (CH), 108.50 (CH), 62.73 ($CH_2$), 53.89 ($CH_2$), 50.51 (C), 45.57 ($CH_2$), 43.37 ($CH_2$), 36.23 (CH), 30.61 ($CH_2$), 29.48 ($CH_2$), 28.93 ($CH_3$), 28.76 ($CH_2$), 22.57 ($CH_2$), 14.08 ($CH_3$). ESI: m/z 491.2 (M+H)$^+$. HRMS calcd for $C_{30}H_{43}N_4O_2$ (M+H)$^+$ 491.3386, found 491.3433.

N-tert-butyl-2-[4-(9-pentyl-9H-carbazole-3-carbonyl)piperazin-1-yl]acetamide (10)

Under argon atmosphere, to a solution of tert-Butyl 4-(9-pentyl-9H-carbazole-3-carbonyl)piperazine-1-carboxylate 8[6] (360 mg, 1.03 mmol) and MeCN (10 mL) was added $K_2CO_3$ (427 mg, 3.09 mmol), KI (160 mg, 0.96 mmol) and N-tert-butyl-2-chloroacetamide (185 mg, 1.24 mmol). The reaction mixture was stirred at reflux for 3 h. The reaction mixture was cooled, diluted with DCM (30 mL), and filtered. The organic solvents were evaporated in vacuo. The organic layer was washed three times with brine (50 mL). The organic layer was then separated, dried over magnesium sulfate, filtered, and concentrated in vacuo. The crude product was purified by flash chromatography eluting with heptane/EtOAc (0-100%) to yield the title compound (437 mg, 92%) as yellow foam. $^1$H NMR (400 MHz, $CDCl_3$) δ 8.19 (d, J=1.24 Hz, 1H), 8.09 (d, J=7.66 Hz, 1H), 7.38-7.55 (m, 4H), 7.23-7.28 (m, 1H), 6.96 (s, 1H), 4.30 (t, J=7.24 Hz, 2H), 3.74 (br. s., 4H), 2.96 (s, 2H), 2.58 (br. s., 4 H), 1.86 (br. s., 2H), 1.24-1.39 (m, 13H), 0.81-1.01 (m, 3H). $^{13}$C NMR (101 MHz, $CDCl_3$) d ppm 171.69 (C=O), 168.71 (C=O), 141.20 (C), 140.94 (C), 126.30 (CH), 125.60 (C), 125.19 (CH), 122.61 (C), 122.50 (C), 120.54 (CH), 120.14 (CH), 119.43 (CH), 109.07 (CH), 108.51 (CH), 77.44 ($CH_2$), 77.33 ($CH_2$), 77.13 ($CH_2$), 76.81 ($CH_2$), 62.27 ($CH_2$), 53.48 ($CH_2$), 50.64 (C), 43.24 ($CH_2$), 29.38 ($CH_2$), 28.83 ($CH_2$), 28.66 ($CH_3$), 22.48 ($CH_2$), 13.98 ($CH_3$). m/z 463.2 (M+H)+. HRMS calcd for $C_{30}H_{43}N_4O_2$ (M+H)+ 463.3073, found 463.2819.

tert-butyl 4-((9-propyl-9H-carbazole-3-carboxamido)methyl)-piperidine-1-carboxylate (11)

9-propyl-9H-carbazole-3-carboxylic acid[6] (100 mg, 0.40 mmol), HOBt (62.32 mg, 0.48 mmol), DIPEA (0.13 mL, 0.79 mmol), DMAP (58.12 mg, 0.40 mmol), and EDAC (91.22 mg, 0.40 mmol) were added upon stirring to DCM (9 mL) under nitrogen. The obtained solution was cooled down on an ice-water bath and tert-Butyl 4-(aminomethyl) piperidine-1-carboxylate (119.24 mg, 0.40 mmol) was added in one portion, and the resulting reaction mixture was then allowed to warm to room temperature and stirred for 16 h. The solvent was removed in vacuo, and the obtained residue was extracted with EtOAc (50 mL). The organic layer was washed three times with brine (25 mL). The organic layer was then separated, dried over magnesium sulfate, filtered, and concentrated in vacuo. The crude product was purified by flash chromatography eluting with heptane/EtOAc (0-100%) to produce the title compound 11 (158.3 mg, 89%) as yellow oil. $^1$H NMR (400 MHz, $CDCl_3$) δ 8.57 (d, J=1.36 Hz, 1H), 8.06 (d, J=7.9 Hz, 1H), 7.89 (dd, J=8.7, 1.67 Hz, 1.11H), 7.44 (ddd, J=8.37, 7.15, 1.2 Hz, 1.1H), 7.31 (d, J=8.2 Hz, 1.0H), 7.27 (d, J=8.7 Hz, 1H), 7.19 (ddd, J=8.06, 7.1, 1.0 Hz, 1H), 6.55 (t, J=5.8 Hz, 1H), 4.26 (t, J=7.2 Hz, 2H), 3.38 (t, J=6.2 Hz, 2H), 3.10 (d, J=12.1 Hz, 2H), 2.61 (td, J=12.2, 2.5 Hz, 2H), 1.99 (s, 1H), 1.97-1.80 (m, 2H), 1.80-1.70 (m, 3H), 1.45 (s, 9H), 1.22 (qd, J=12.8, 3.7 Hz, 2H), 0.97 (t, J=7.4 Hz, 3H). $^{13}$C (101 MHz, CDCl$_3$) δ 168.53, 154.77, 142.30, 141.16, 126.42, 125.42, 124.77, 122.97, 122.74, 120.74, 119.83, 119.68, 109.22, 108.53, 79.22, 45.22, 45.39, 36.91, 31.38, 28.41, 22.58, 12.10.

9-Propyl-N-(piperidin-4-ylmethyl)-9H-carbazole-3-carboxamide (12)

Trifluoroacetic acid (5 mL) was added to a solution of 11 (150 mg, 0.33 mmol) in CH$_2$Cl$_2$ (5 mL), and the reaction mixture was stirred at room temperature for 4 h. The mixture was evaporated, and the residue was basified with 2 N NaOH. The solution was extracted with CH$_2$Cl$_2$ three times. The extracts were dried with Na$_2$SO$_4$ and evaporated. The crude product was purified by flash chromatography eluting with heptane/EtOAc (0-100%) to produce the title compound 12 (95.5 mg, 83%) as dark yellow oil. $^1$H NMR (400 MHz, CDCl$_3$) δ 8.56 (d, J=1.4 Hz, 1H), 8.05 (d, J=7.9 Hz, 1H), 7.90 (dd, J=8.7, 1.7 Hz, 1.1H), 7.5 (ddd, J=8.4, 7.2, 1.2 Hz, 1.1H), 7.31 (d, J=8.2 Hz, 1.0H), 7.28 (d, J=8.7 Hz, 1H), 7.17 (ddd, J=8.0, 7.1, 1.0 Hz, 1H), 6.58 (t, J=5.8 Hz, 1H), 4.25 (t, J=7.1 Hz, 2H), 3.39 (t, J=6.2 Hz, 2H), 3.09 (d, J=12.1 Hz, 2H), 2.60 (td, J=12.2, 2.5 Hz, 2H), 1.99 (s, 1H), 1.98-1.80 (m, 2H), 1.80-1.71 (m, 3H), 1.23 (qd, J=12.8, 3.7 Hz, 2H), 0.96 (t, J=7.5 Hz, 3H). $^{13}$C (101 MHz, CDCl$_3$) δ 168.51, 142.32, 141.15, 126.40, 125.41, 124.79, 122.99, 122.73, 120.73, 119.82, 119.67, 109.21, 108.50, 46.47, 46.20, 45.37, 36.91, 31.37, 22.59, 12.10.

N-((1-(2-(tert-butylamino)-2-oxoethyl)piperidin-4-yl)methyl)-9-propyl-9H-carbazole-3-carboxamide (13)

Under argon atmosphere, to a solution of 12 (90 mg, 0.26 mmol) and MeCN (2.5 mL) was added K$_2$CO$_3$ (107.8 mg, 0.78 mmol), KI (43.2 mg, 0.26 mmol) and N-tert-butyl-2-chloroacetamide (47.9 mg, 0.32 mmol). The title compound was prepared according to the analogous procedure described above for compound 9 to produce the title compound 13 (121.3 mg, 82%) as dark yellow oil. $^1$H NMR (400 MHz, CDCl3) δ 8.56 (d, J=1.39 Hz, 1H), 8.05 (d, J=8 Hz, 1H), 7.91 (dd, J=8.7, 1.6 Hz, 1H), 7.44 (ddd, J=8.3, 7.1, 1.2 Hz, 1H), 7.31 (d, J=8.2 Hz, 1H), 7.28 (d, J=8.7 Hz, 1H), 7.17 (ddd, J=8.1, 7.1, 1.0 Hz, 1H), 6.98 (br s, 1H), 6.58 (t, J=5.8 Hz, 1H), 4.26 (t, J=7.1 Hz, 2H), 3.33 (t, J=6.3 Hz, 2H), 2.82-2.67 (m, 4H), 2.03 (td, J=11.8, 2.7 Hz, 2H), 1.86-1.76 (m, 2H), 1.7 (d, J=13.7 Hz, 2H), 1.64-1.48 (m, 1H), 1.34 (s, 9H), 0.94 (t, J=7 Hz, 3H). $^{13}$C and DEPT NMR (101 MHz, CDCl3) δ 169.84 (C=O), 168.5 (C=O), 142.34 (C), 141.17 (C), 126.41 (CH), 126.0 (C), 124.79 (CH), 122.94 (C), 122.71 (C), 120.68 (CH), 119.84 (CH), 119.69 (CH), 109.23 (CH), 108.51 (CH), 62.74 (CH$_2$), 53.9 (CH$_2$), 50.52 (C), 45.58 (CH$_2$), 45.35 (CH$_2$), 36.22 (CH), 30.61 (CH$_2$), 28.90 (CH$_3$), 22.76 (CH$_2$), 12.18 (CH$_3$). ESI: m/z 463.3 (M+H)+. HRMS calcd for C$_{28}$H$_{40}$N$_4$O$_2$ (M+H)+, 463.3073 found 463.3089.

Tert-butyl 4-((9-butyl-9H-carbazole-3-carboxamido)methyl) piperidine-1-carboxylate (14)

Using 9-butyl-9H-carbazole-3-carboxylic acid[6] (100 mg, 0.37 mmol), HOBt (60.54 mg, 0.45 mmol), DIPEA (0.13 mL, 0.75 mmol), DMAP (54.73 mg, 0.45 mmol), tert-Butyl 4-(aminomethyl) piperidine-1-carboxylate (112.22 mg, 0.45 mmol) and EDAC (85.85 mg, 0.45 mmol), the title compound was prepared according to the analogous procedure described above for compound 11, to produce the title compound 14 (147.3 mg, 85%) as a yellow oil. $^1$H NMR (400 MHz, CDCl$_3$) δ 8.53 (d, J=1.33 Hz, 1H), 8.04 (d, J=7.82 Hz, 1H), 7.82 (dd, J=8.6, 1.7 Hz, 1H), 7.43 (ddd, J=8.4, 7.14, 1.22 Hz, 1H), 7.31 (d, J=8.22 Hz, 1H), 7.27 (d, J=8.61 Hz, 1H), 7.16 (ddd, J=8.02, 7.1, 1.0 Hz, 1H), 6.57 (t, J=5.8 Hz, 1H), 4.24 (t, J=7.2 Hz, 2H), 3.37 (t, J=6.2 Hz, 2H), 3.07 (d, J=12.1 Hz, 2H), 2.61 (td, J=12.2, 2.5 Hz, 2H), 2.00 (s, 1H), 1.98-1.80 (m, 2H), 1.80-1.71 (m, 3H), 1.45 (s, 9H), 1.43-1.32 (m, 2H), 1.23 (qd, J=12.8, 3.7 Hz, 2H), 0.90 (t, J=7.4 Hz, 3H). $^{13}$C (101 MHz, CDCl$_3$) δ 168.50, 154.75, 142.33, 141.16, 126.45, 125.43, 124.80, 122.97, 122.72, 120.73, 119.81, 119.68, 109.21, 108.50, 79.26, 45.47, 43.04, 36.90, 31.36, 28.41, 20.78, 14.13.

9-butyl-N-piperidin-4-ylmethyl)-9H-carbazole-3-carboxamide (15)

Trifluoroacetic acid (5 mL) was added to a solution of 14 (140 mg, 0.30 mmol) in CH$_2$Cl$_2$ (5 mL), the title compound was prepared according to the analogous procedure described above for compound 12 to produce the title compound 15 (95.7 mg, 88%) as dark yellow oil. $^1$H NMR (400 MHz, CDCl$_3$) δ 8.53 (d, J=1.3 Hz, 1H), 8.02 (d, J=7.8 Hz, 1H), 7.84 (dd, J=8.6, 1.7 Hz, 1H), 7.41 (ddd, J=8.4, 7.2, 1.2 Hz, 1H), 7.30 (d, J=8.2 Hz, 1H), 7.27 (d, J=8.7 Hz, 1H), 7.17 (ddd, J=8.0, 7.1, 1.0 Hz, 1H), 6.58 (t, J=5.8 Hz, 1H), 4.25 (t, J=7.2 Hz, 2H), 3.39 (t, J=6.2 Hz, 2H), 3.09 (d, J=12.2 Hz, 2H), 2.60 (td, J=12.2, 2.5 Hz, 2H), 1.99 (s, 1H), 1.98-1.80 (m, 2H), 1.80-1.71 (m, 3H), 1.43-1.32 (m, 2H), 1.23 (qd, J=12.8, 3.7 Hz, 2H), 0.90 (t, J=7.4 Hz, 3H). $^{13}$C (101 MHz, CDCl$_3$) δ 168.51, 142.32, 141.15, 126.45, 125.41, 124.79, 122.99, 122.73, 120.73, 119.82, 119.67, 109.21, 108.50, 46.47, 46.20, 43.03, 36.91, 31.37, 20.79, 14.12.

N-((1-(2-(tert-butylamino)-2-oxoethyl)piperidin-4-yl)methyl)-9-butyl-9H-carbazole-3-carboxamide (16)

Under argon atmosphere, to a solution of 15 (90 mg, 0.25 mmol) and MeCN (2.5 mL) was added K$_2$CO$_3$ (103.7 mg, 0.75 mmol), KI (41.5 mg, 0.25 mmol) and N-tert-butyl-2-chloroacetamide (44.9 mg, 0.30 mmol). The title compound was prepared according to the analogous procedure described above for compound 9 to produce the title compound 16 (99.9 mg, 84%) as dark yellow oil. $^1$H NMR (400 MHz, CDCl$_3$) δ 8.50 (d, J=1.3 Hz, 1H), 8.01 (d, J=7.8 Hz, 1H), 7.8 (dd, J=8.6, 1.7 Hz, 1H), 7.4 (ddd, J=8.4, 7.13, 1.22 Hz, 1H), 7.30 (d, J=8.2 Hz, 1H), 7.27 (d, J=8.5 Hz, 1H), 7.16 (ddd, J=8.1, 7.0, 1.0 Hz, 1H), 7.01 (br s, 1H), 6.57 (t, J=5.8 Hz, 1H), 4.24 (t, J=7.2 Hz, 2H), 3.35 (t, J=6.5 Hz, 2H), 2.83-2.68 (m, 4H), 2.00 (td, J=11.7, 2.5 Hz, 2H), 1.82-1.72 (m, 2H), 1.73 (d, J=13.8 Hz, 2H), 1.63-1.49 (m, 1H), 1.45-1.34 (m, 2H), 1.33 (s, 9H), 0.90 (t, J=6.87 Hz, 3H). $^{13}$C and DEPT NMR (101 MHz, CDCl$_3$) δ 169.83 (C=O), 168.57 (C=O), 142.34 (C), 141.14 (C), 126.45 (CH), 125.26 (C), 124.82 (CH), 122.94 (C), 122.73 (C), 120.68 (CH), 119.85 (CH), 119.68 (CH), 109.21 (CH), 108.50 (CH), 62.71 (CH$_2$), 53.90 (CH$_2$), 50.50 (C), 45.59 (CH$_2$), 43.00 (CH$_2$), 36.26 (CH), 30.66 (CH$_2$), 29.43 (CH$_2$), 28.92 (CH$_3$), 20.74 (CH2), 14.10 (CH3). ESI: m/z 477.2 (M+H)+. HRMS calcd for C$_{29}$H$_{41}$N$_4$O$_2$ (M+H)+ 477.3229, found 477.3217.

Tert-butyl 4-((9-pentyl-9H-carbazole-3-carboxamido)methyl)pyrrolidine-1-carboxylate (17)

Using 9-pentyl-9H-carbazole-3-carboxylic acid (100 mg, 0.36 mmol), [6] HOBt (57.81 mg, 0.43 mmol), DIPEA (0.12 mL, 0.71 mmol), DMAP (52.29 mg, 0.43 mmol), (R)-3-(Aminomethyl)-1-Boc-pyrrolidine (85.66 mg, 0.43 mmol) and EDAC (82.02 mg, 0.43 mmol), the title compound was prepared according to the analogous procedure described above for compound 11 using the amide coupling protocol, to produce the title compound 17 (141.8 mg, 86%) as a yellow oil. $^1$H NMR (400 MHz, CDCl$_3$) δ 8.58 (d, J=1.4 Hz, 1H), 8.02 (d, J=7.8 Hz, 1H), 7.83 (dd, J=8.6, 1.7 Hz, 1H), 7.42 (ddd, J=8.4, 7.14, 1.23 Hz, 1H), 7.31 (d, J=8.22 Hz, 1H), 7.28 (d, J=8.61 Hz, 1H), 7.17 (ddd, J=8.1, 7.10, 1.0 Hz, 1H), 6.57 (t, J=5.84 Hz, 1H), 4.16 (t, J=7.2 Hz, 2H), 3.22-3.12 (m, 2H), 2.34-2.21 (m, 2H), 2.12-1.98 (m, 1H), 1.81-1.67 (m, 3H), 1.45 (s, 9H), 1.38-1.20 (m, 4H), 0.80 (t, J=6.9 Hz, 3H). $^{13}$C (101 MHz, CDCl$_3$) δ 168.56, 154.75, 142.32, 141.13, 126.47, 125.25, 124.82, 122.92, 122.72, 120.69, 119.85, 119.68, 109.22, 108.50, 79.27, 54.28, 45.50, 39.78, 38.75, 36.26, 30.68, 29.45, 28.42, 20.75, 14.10.

9-Pentyl-N-(pyrrolidin-4-ylmethyl)-9H-carbazole-3-carboxamide (18)

Trifluoroacetic acid (5 mL) was added to a solution of compound 17 (135 mg, 0.29 mmol) in CH$_2$Cl$_2$ (5 mL), the title compound was prepared according to the analogous procedure described above for compound 12 to produce the title compound 18 (90.7 mg, 86%) as yellow oil. $^1$H NMR (400 MHz, CDCl$_3$) δ 8.57 (d, J=1.4 Hz, 1H), 8.03 (d, J=7.8 Hz, 1H), 7.84 (dd, J=8.6, 1.7 Hz, 1H), 7.41 (ddd, J=8.4, 7.13, 1.22 Hz, 1H), 7.32 (d, J=8.22 Hz, 1H), 7.27 (d, J=8.61 Hz, 1H), 7.17 (ddd, J=8.1, 7.10, 1.0 Hz, 1H), 6.57 (t, J=5.84 Hz, 1H), 4.16 (t, J=7.2 Hz, 2H), 3.22-3.13 (m, 2H), 2.34-2.22 (m, 2H), 2.12-1.99 (m, 1H), 1.82-1.68 (m, 3H), 1.38-1.20 (m, 4H), 0.82 (t, J=6.9 Hz, 3H). $^{13}$C (101 MHz, CDCl$_3$) δ 168.55, 142.33, 141.14, 126.46, 125.24, 124.82, 122.93, 122.72, 120.69, 119.85, 119.68, 109.22, 108.50, 54.27, 45.50, 39.79, 38.76, 36.26, 30.68, 29.44, 20.76, 14.11.

N-((1-(2-(tert-butylamino)-2-oxoethyl)pyrrolidin-4-yl)methyl)-9-pentyl-9H-carbazole-3-carboxamide (19)

Under argon atmosphere, to a solution of compound 18 (85 mg, 0.23 mmol) and MeCN (2.5 mL) was added K$_2$CO$_3$ (95.4 mg, 0.69 mmol), KI (38.1 mg, 0.69 mmol) and N-tert-butyl-2-chloroacetamide (41.9 mg, 0.28 mmol). The title compound was prepared according to the analogous procedure described above for compound 10 to produce the title compound 19 (96.2 mg, 88%) as dark yellow oil. $^1$H NMR (400 MHz, CDCl$_3$) δ 8.58 (d, J=1.4 Hz, 1H), 8.02 (d, J=7.8 Hz, 1H), 7.83 (dd, J=8.6, 1.7 Hz, 1H), 7.41 (ddd, J=8.4, 7.13, 1.22 Hz, 1H), 7.31 (d, J=8.22 Hz, 1H), 7.27 (d, J=8.61 Hz, 1H), 7.16 (ddd, J=8.1, 7.10, 1.0 Hz, 1H), 7.01 (br s, 1H), 6.56 (t, J=5.84 Hz, 1H), 4.16 (t, J=7.2 Hz, 2H), 3.22-3.11 (m, 4H), 2.34-2.22 (m, 2H), 2.11-1.99 (m, 1H), 1.81-1.67 (m, 3H), 1.39-1.22 (m, 16H), 0.83 (t, J=6.9 Hz, 3H). $^{13}$C and DEPT NMR (101 MHz, CDCl$_3$) δ 169.83 (C=O), 168.57 (C=O), 142.34 (C), 141.14 (C), 126.45 (CH), 125.26 (C), 124.82 (CH), 122.94 (C), 122.73 (C), 120.68 (CH), 119.85 (CH), 119.68 (CH), 109.21 (CH), 108.50 (CH), 63.41 (CH$_2$), 60.41 (CH$_2$), 55.56 (CH$_2$), 50.89 (C), 47.36 (CH$_2$), 44.07 (CH$_2$), 36.67 (CH), 30.46 (CH$_2$), 29.53 (CH$_2$), 28.88 (CH$_3$), 20.58 (CH$_2$), 14.14 (CH$_3$). ESI: m/z 477.5 (M+H)+. HRMS calcd for C$_{29}$H$_{41}$N$_4$O$_2$ (M+H)+ 477.3229, found 477.3251.

N-{[1-(3,3-dimethylbutyl)piperidin-4-yl]methyl}-9-pentyl-9H-carbazole-3-carboxamide (20)

9-Pentyl-9H-carbazole-3-carboxylic acid[6] (100 mg, 0.27 mmol) was combined with cyanoborohydride (83.3 mg, 1.35 mmol/g), 3,3-dimethylbutyraldehyde (0.06 mL, 0.31 mmol) and suspended in anhydrous CH$_2$Cl$_2$ (2 mL). The mixture was stirred at room temperature overnight. The reaction mixture was diluted with DCM (30 mL), and organic layer was washed three times with brine (50 mL). The organic layer was then separated, dried over magnesium sulfate, filtered, and concentrated in vacuo. The crude product was purified by flash chromatography eluting with heptane/EtOAc (0-100%) to yield the title compound (88.4 mg, 71%). 1H NMR (400 MHz, CDCl$_3$) δ 8.51 (d, J=1.3 Hz, 1H), 8.04 (d, J=7.7 Hz, 1H), 7.86 (dd, J=8.6, 1.6 Hz, 1H), 7.42 (ddd, J=8.3, 7.1, 1.2 Hz, 1H), 7.35 (d, J=8.2 Hz, 1H), 7.29 (d, J=8.6 Hz, 1H), 7.15 (ddd, J=8.0, 7.1, 1.0 Hz, 1H), 7.01 (br s, 1H), 6.59 (t, J=5.8 Hz, 1H), 4.20 (t, J=7.2 Hz, 2H), 3.36 (t, J=6.5 Hz, 2H), 2.69-2.54 (m, 4H), 2.01 (td, J=11.7, 2.5 Hz, 2H), 1.83-1.74 (m, 4H), 1.64-1.48 (m, 1H), 1.33-1.23 (m, 8H), 0.91 (s, 9H), 0.77 (t, J=6.9 Hz, 3H). 13C and DEPT NMR (101 MHz, CDCl3) δ 168.76 (C=O), 142.47 (C), 141.23 (C), 126.67 (CH), 125.48 (C), 124.18 (CH), 122.76 (C), 122.53 (C), 120.68 (CH), 119.85 (CH), 119.68 (CH), 109.23 (CH), 108.50 (CH), 53.89 (CH$_2$), 52.31 (CH$_2$), 45.67 (CH$_2$), 43.42 (CH$_2$), 40.22 (CH$_2$), 36.21 (CH), 30.54 (CH$_2$), 30.12 (C), 29.42 (CH$_2$), 29.34 (CH$_3$), 28.71 (CH$_2$), 22.56 (CH$_2$), 14.03 (CH$_3$). ESI: m/z 462.3 (M+H)+. HRMS calcd for C$_{30}$H$_{43}$N$_3$O (M+H)+462.3484, found 462.3452.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

CITED REFERENCES (1) Jagodic, M. M., et al., *Cell-specific alterations of T-type calcium current in painful diabetic neuropathy enhance excitability of sensory neurons*. J Neurosci, 2007. 27(12): p. 3305-16. (2) Barton, M. E., E. L. Eberle, and H. E. Shannon, *The antihyperalgesic effects of the T-type calcium channel blockers ethosuximide, trimethadione, and mibefradil*. Eur J Pharmacol, 2005. 521(1-3): p. 79-85. (3) Bourinet, E., et al., *Silencing of the Cav3.2 T-type calcium channel gene in sensory neurons demonstrates its major role in nociception*. EMBO J, 2005. 24(2): p. 315-24. (4) Choi, S., et al., *Attenuated pain responses in mice lacking Ca(V)3.2 T-type channels*. Genes Brain Behav, 2007. 6(5): p. 425-31. (5) Dogrul, A., et al., *Reversal of experimental neuropathic pain by T-type calcium channel blockers*. Pain, 2003. 105(1-2): p. 159-68. (6) Gadotti, V. M., et al., *Analgesic effect of a mixed T-type channel inhibitor/CB2 receptor agonist*. Mol Pain, 2013. 9: p. 32. (7) Jagodic, M. M., et al., *Upregulation of the T-type calcium current in small rat sensory neurons after chronic constrictive injury of the sciatic nerve*. J Neurophysiol, 2008. 99(6): p. 3151-6. (8) Obradovic, A., et al., *CaV3.2

T-Type Calcium Channels in Peripheral Sensory Neurons Are Important for Mibefradil-Induced Reversal of Hyperalgesia and Allodynia in Rats with Painful Diabetic Neuropathy. PLoS One, 2014. 9(4): p. e91467. (9) You, H., et al., Functional characterization and analgesic effects of mixed cannabinoid receptor/T-type channel ligands. Mol Pain, 2011. 7: p. 89. (10) Petrov, R. R., et al., Mastering tricyclic ring systems for desirable functional cannabinoid activity. Eur J Med Chem, 2013. 69: p. 881-907. (11) Marger, F., et al., T-type calcium channels contribute to colonic hypersensitivity in a rat model of irritable bowel syndrome. Proc Natl Acad Sci USA, 2011. 108(27): p. 11268-73.

What is claimed is:

1. A compound of the formula:

I wherein
$R^1$ is alkyl;
X is selected from the group consisting of —C(=O)—[NR$^4$]$_a$—, —C(=S)—, and —S(=O)$_b$—;
$R^2$ is selected from the group consisting of piperidinyl and pyrrolidinyl;
$R^3$ is selected from the group consisting of —C(=O)NH-tBu and 3,3-dimethylbutyl;
$R^4$ is hydrogen, alkyl, or a nitrogen protecting group;
a is 0 or 1;
b is 1 or 2;
n=1 to 3; and
m=0 to 1.

2. The compound of claim 1, wherein $R^1$ is selected from the group consisting of $C_1$-$C_{10}$ alkyl.

3. The compound of claim 2, wherein $R^1$ is propyl, butyl, or pentyl.

4. The compound of claim 1, wherein X is —C(=O)—NH—.

5. The compound of claim 4, wherein n is 1.

6. The compound of claim 1, wherein $R^2$ is selected from the group consisting of 7. The compound of claim 4, wherein m is 1.

8. The compound of claim 4, wherein $R^3$ is —C(=O)NH-tBu.

9. The compound of claim 8, wherein $R^3$ is 3,3-dimethylbutyl.

10. The compound of claim 1, wherein $R^1$ is selected from the group consisting of propyl, butyl and pentyl.

11. A method for treating a clinical condition associated with T-type calcium channel activation, said method comprising administering to a subject in need of such a treatment a therapeutically effective amount of a compound of claim 1 wherein treating does not embrace preventing.

12. The method of claim 11, wherein said clinical condition associated with T-type calcium channel activation comprises acute inflammatory pain, tactile allodynia, diabetic neuropathy, pulmonary hypertension, chemotherapeutic induced neuropathy, chronic pain, diabetes, epilepsy, visceral pain, cancer pain, cardiac hypertrophy, or a combination thereof.

13. A method for treating a clinical condition associated with T-type calcium channel activation, said method comprising administering to a subject in need of such a treatment a therapeutically effective amount of a compound selected from the group consisting of:

wherein treating does not embrace preventing.

* * * * *